(12) United States Patent
Campbell (10) Patent No.: US 10,797,357 B2
(45) Date of Patent: Oct. 6, 2020

(54) SYSTEMS AND METHODS FOR EXTENDING A SHELF LIFE OF A RECHARGEABLE BATTERY ASSEMBLY

(71) Applicant: Advanced Bionics AG, Staefa (CH)

(72) Inventor: Geoffrey Campbell, Castaic, CA (US)

(73) Assignee: Advanced Bionics AG, Staefa (CH)

( * ) Notice: Subject to any disclaimer, the term of this patent is extended or adjusted under 35 U.S.C. 154(b) by 0 days.

(21) Appl. No.: 16/343,744

(22) PCT Filed: Sep. 28, 2017

(86) PCT No.: PCT/US2017/054126
§ 371 (c)(1),
(2) Date: Apr. 19, 2019

(87) PCT Pub. No.: WO2018/075212
PCT Pub. Date: Apr. 26, 2018

(65) Prior Publication Data
US 2019/0280342 A1    Sep. 12, 2019

Related U.S. Application Data

(60) Provisional application No. 62/411,296, filed on Oct. 21, 2016.

(51) Int. Cl.
*H01M 10/42* (2006.01)
*A61N 1/36* (2006.01)
(Continued)

(52) U.S. Cl.
CPC ...... *H01M 10/425* (2013.01); *A61N 1/36038* (2017.08); *H01M 10/0525* (2013.01);
(Continued)

(58) Field of Classification Search
None
See application file for complete search history.

(56) References Cited

U.S. PATENT DOCUMENTS

| 5,804,944 A | 9/1998 | Alberkrack et al. |
| 8,283,899 B2 | 10/2012 | Esnard et al. |

(Continued)

FOREIGN PATENT DOCUMENTS

| GB | 2279802 | 1/1995 |
| WO | 2014/112982 | 7/2014 |

OTHER PUBLICATIONS

International Search Report and Written Opinion received in International Application No. PCT/US17/054126, dated Nov. 14, 2017.

*Primary Examiner* — Wojciech Haske
(74) *Attorney, Agent, or Firm* — ALG Intellectual Property, LLC (57) ABSTRACT

An exemplary battery assembly includes a rechargeable battery cell that has a state of charge, a safety circuit configured to transition the battery assembly to a power-down mode when the state of charge of the rechargeable battery cell is less than a predetermined threshold state of charge, and a hibernation control network. The hibernation control network 1) detects, by way of a phototransistor while the state of charge is greater than the predetermined threshold state of charge, a light beam having a predetermined wavelength, and 2) triggers, in response to the detecting of the light beam of the predetermined wavelength and while the state of charge of the rechargeable battery is still greater than the predetermined threshold state of charge, the safety circuit to transition the battery assembly to the power-down mode.

13 Claims, 3 Drawing Sheets

(51) Int. Cl.
 *H01M 10/0525* (2010.01)
 *A61N 1/05* (2006.01)
(52) U.S. Cl.
 CPC ....... *A61N 1/0541* (2013.01); *H01M 2200/00* (2013.01); *H01M 2200/20* (2013.01); *H01M 2220/30* (2013.01)

(56) References Cited

U.S. PATENT DOCUMENTS

| | | |
|---|---|---|
| 8,571,608 B2 | 10/2013 | Esnard et al. |
| 9,142,983 B2 | 9/2015 | Kitajima et al. |
| 9,184,608 B2 | 11/2015 | Esnard et al. |
| 9,343,226 B2 | 5/2016 | Esnard-Domerego et al. |
| 2010/0320969 A1* | 12/2010 | Sakakibara ......... H01M 2/1022 320/118 |
| 2014/0210420 A1* | 7/2014 | Lee ....................... H02J 7/0068 320/134 |

* cited by examiner

SYSTEMS AND METHODS FOR EXTENDING A SHELF LIFE OF A RECHARGEABLE BATTERY ASSEMBLY

RELATED APPLICATIONS

The present application claims priority to U.S. Provisional Patent Application No. 62/411,296, filed Oct. 21, 2016. The contents of the provisional patent application are hereby incorporated by reference in their entirety.

BACKGROUND INFORMATION

Rechargeable lithium-ion batteries have revolutionized the portable electronics industry, including the medical device sector. Such batteries generally have a higher energy density, lower self-discharge rate, and smaller memory effect than similar batteries that employ other rechargeable battery technologies (e.g., conventional nickel-metal hydride battery cells, nickel-cadmium battery cells, etc.). Rechargeable lithium-ion batteries have proven to be useful for many applications in the medical device industry including, for example, providing power to sound processors included in cochlear implant systems.

Unfortunately, lithium-ion batteries have several limitations. For example, a lithium-ion battery may become damaged if it is allowed to discharge below a critical state of charge threshold for more than a short period of time. To prevent such damage, a lithium-ion battery assembly may include a safety circuit configured to transition the battery assembly to a power-down mode (e.g., disconnect a depleted cell in the lithium-ion battery from an output or load) if the lithium-ion battery's state of charge drops below a predetermined safe range (e.g., below five percent).

Such a safety circuit may use power from the lithium-ion battery to monitor a state of charge of the lithium-ion battery, even during periods when the lithium-ion battery is not being used to power an electronic device (e.g., while the lithium-ion battery is in storage prior to use). This monitoring, as well as other factors, may contribute to a self-discharge rate of the lithium-ion battery, where the lithium-ion battery may continually lose a small amount of charge even during periods of non-use. Consequently, an unused lithium-ion battery (e.g., a lithium-ion battery maintained in an inventory before it is inserted into a sound processor included in a cochlear implant system) may require periodic charging to avoid dropping below a critical state of charge threshold. Often, an unused lithium-ion battery must be returned by a distributor to a manufacturer to conduct the charging and to recertify that the battery meets certain standards. This required periodic recharging and/or recertification process may significantly increase a cost of maintaining a lithium-ion battery inventory for lithium-ion battery manufacturers, suppliers, and/or distributors.

The above limitations have been exacerbated by recent developments in lithium-ion battery miniaturization techniques. For example, certain new lithium-ion batteries, designed for use in sound processors included in cochlear implant systems, may have small charge capacities (e.g., less than 100 mAh). Such small capacity batteries—even when fully charged by a manufacturer before shipping to a distributor or customer—may have a relatively short predicted shelf life, due primarily to a constant discharge of the battery's lithium-ion cell by a perpetually active safety circuit. Hence, these small capacity lithium-ion batteries may require more frequent recharging and/or recertification, which could lead to even more costs to manufacturers, suppliers, distributors, etc. who maintain inventories of these small capacity lithium-ion batteries.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Systems and methods for extending a shelf life of a rechargeable battery assembly are disclosed herein. For example, an exemplary battery assembly may include a rechargeable battery cell, a safety circuit, and a hibernation circuit. Each of these components will now be briefly described.

The rechargeable battery cell may be configured to provide operating power to a component (e.g., a sound processor included in a cochlear implant system) to which the battery assembly is electrically connected. To this end, the rechargeable battery cell may hold or maintain a certain amount of charge, which, as will be described in more detail below, may dissipate over time when the rechargeable battery cell is not being actively charged (e.g., by a battery charger). An amount of charge that a rechargeable battery cell actually has at any given time compared to a maximum amount of charge that the rechargeable battery cell is capable of maintaining will be referred to herein as a "state of charge" of the rechargeable battery cell. For example, a rechargeable battery cell that has an amount of charge that is equal to fifty percent of the maximum amount of charge that the rechargeable battery cell is capable of maintaining has a fifty percent state of charge.

The safety circuit may be electrically coupled to the rechargeable battery cell and configured to transition the battery assembly to a power-down mode when the state of charge of the rechargeable battery cell is less than a predetermined threshold state of charge (e.g., less than ten percent). In this manner, the safety circuit may prevent or minimize the risk of damage to the battery assembly that could occur if the state of charge of the rechargeable battery cell dips below a critical state of charge threshold.

The hibernation control network may be electrically coupled to the safety circuit and configured to trigger, at the direction of an external user, the safety circuit to transition the battery assembly into the power-down mode even if the state of charge of the rechargeable battery cell is above the predetermined threshold state of charge. To this end, the hibernation control network may include a phototransistor configured to detect a light beam having a predetermined wavelength (e.g., a wavelength in the near-infrared region of an electromagnetic spectrum) and emitted by a light source located external to the battery assembly (e.g., a light source operated by a user).

In response to the detection of the light beam of the predetermined wavelength, and while the state of charge of the rechargeable battery cell is still greater than the predetermined threshold state of charge (e.g., greater than ten percent), the hibernation control network may trigger the safety circuit to transition the battery assembly to the power-down mode. In this manner, the hibernation control network may "trick" the safety circuit into transitioning the battery assembly to the power-down mode. Because, as will be described in more detail below, various current-drawing components within the battery assembly are in a disabled state while the battery assembly is in the power-down mode, a self-discharge rate (i.e., a rate at which charge dissipates from the rechargeable battery cell due to current being drawn by active components within the battery assembly) may be reduced. This, in turn, extends a shelf life of the battery assembly (i.e., an amount of time that the battery assembly may go without having to be recharged or used may be increased). By extending the shelf life of the battery assembly in this manner, the systems and methods described herein may minimize or eliminate a need for the battery assembly to be recharged and/or recertified before the battery assembly is used in production (i.e., used to provide power for a product, such as a sound processor included in a cochlear implant system).

Hence, the systems and methods described herein may reduce cost and effort associated with maintaining rechargeable battery inventories.

Figure 1:
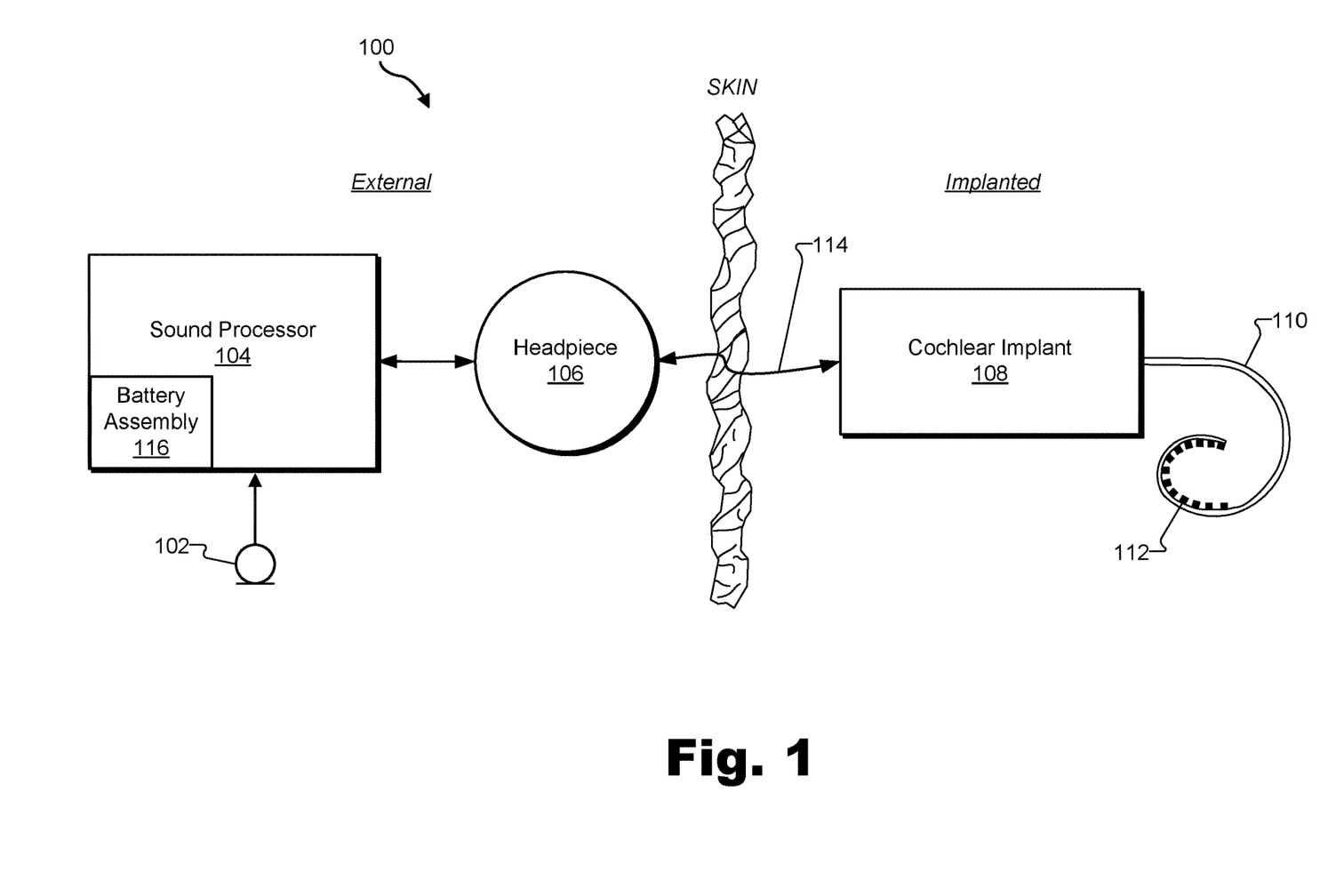
FIG. 1 illustrates an exemplary audio prosthesis system according to principles described herein.

A battery assembly according to the principles described herein may be included in a device that requires electrical power to operate, such as an audio prosthesis system (e.g., a cochlear implant system). For example, FIG. 1 illustrates an exemplary audio prosthesis system 100. Auditory prosthesis system 100 may include a microphone 102, a sound processor 104, a headpiece 106 having a coil disposed therein, a cochlear implant 108, and an electrode lead 110 (also referred to as a "lead"). Lead 110 includes an array of intracochlear electrodes 112 disposed on a distal portion of lead 110 and that are configured to be located within the cochlea after the lead 110 is inserted into the cochlea. Additional or alternative components may be included within auditory prosthesis system 100 as may serve a particular implementation.

As shown, auditory prosthesis system 100 may include various components configured to be located external to a patient including, but not limited to, microphone 102, sound processor 104, and headpiece 106. Auditory prosthesis system 100 may further include various components configured to be implanted within the patient including, but not limited to, cochlear implant 108 and electrode lead 110.

Microphone 102 may be configured to detect audio signals presented to the user. Microphone 102 may be implemented in any suitable manner. For example, microphone 102 may include a microphone that is configured to be placed within the concha of the ear near the entrance to the ear canal, such as a T-MIC™ microphone from Advanced Bionics. Such a microphone may be held within the concha of the ear near the entrance of the ear canal by a boom or stalk that is attached to an ear hook configured to be selectively attached to sound processor 104. Additionally or alternatively, microphone 102 may be implemented by one or more microphones disposed within headpiece 106, one or more microphones disposed within sound processor 104, one or more beam-forming microphones, and/or any other suitable microphone as may serve a particular implementation.

Sound processor 104 (i.e., one or more components included within sound processor 104) may be configured to direct cochlear implant 108 to generate and apply electrical stimulation (also referred to herein as "stimulation current") representative of one or more audio signals (e.g., one or more audio signals detected by a microphone, input by way of an auxiliary audio input port, input by way of a CPI, etc.) to one or more stimulation sites associated with an auditory pathway (e.g., the auditory nerve) of the patient. Exemplary stimulation sites include, but are not limited to, one or more locations within the cochlea, the cochlear nucleus, the inferior colliculus, and/or any other nuclei in the auditory pathway. To this end, sound processor 104 may process the one or more audio signals in accordance with a selected sound processing strategy or program to generate appropriate stimulation parameters for controlling cochlear implant 108. Sound processor 104 may be housed within any suitable housing (e.g., a behind-the-ear ("BTE") unit, a body worn device, and/or any other sound processing unit as may serve a particular implementation). In some examples, sound processor 104 may wirelessly transmit stimulation parameters (e.g., in the form of data words included in a forward telemetry sequence) and/or power signals to cochlear implant 108 by way of a wireless communication link 114 between headpiece 106 and cochlear implant 108. It will be understood that communication link 114 may include a bi-directional communication link and/or one or more dedicated uni-directional communication links.

Headpiece 106 may be communicatively coupled to sound processor 104 and may include an external antenna (e.g., a coil and/or one or more wireless communication components) configured to facilitate selective wireless coupling of sound processor 104 to cochlear implant 108. Headpiece 106 may additionally or alternatively be used to selectively and wirelessly couple any other external device to cochlear implant 108. To this end, headpiece 106 may be configured to be affixed to the patient's head and positioned such that the external antenna housed within headpiece 106 is communicatively coupled to a corresponding implantable antenna (which may also be implemented by a coil and/or one or more wireless communication components) included within or otherwise associated with cochlear implant 108. In this manner, stimulation parameters and/or power signals may be wirelessly transmitted between sound processor 104 and cochlear implant 108 via communication link 114.

Cochlear implant 108 may include any type of implantable stimulator that may be used in association with the systems and methods described herein. For example, cochlear implant 108 may be implemented by an implantable cochlear stimulator. In some alternative implementations, cochlear implant 108 may include a brainstem implant and/or any other type of cochlear implant that may be implanted within a patient and configured to apply stimulation to one or more stimulation sites located along an auditory pathway of a patient.

In some examples, cochlear implant 108 may be configured to generate electrical stimulation representative of an audio signal processed by sound processor 104 (e.g., an audio signal detected by microphone 102) in accordance with one or more stimulation parameters transmitted thereto by sound processor 104. Cochlear implant 108 may be further configured to apply the electrical stimulation to one or more stimulation sites (e.g., one or more intracochlear regions) within the patient via one or more intracochlear electrodes 112 disposed along electrode lead 110. In some examples, cochlear implant 108 may include a plurality of independent current sources each associated with a channel defined by one or more of intracochlear electrodes 112. In this manner, different stimulation current levels may be applied to multiple stimulation sites simultaneously by way of multiple intracochlear electrodes 112.

The auditory prosthesis system 100 illustrated in FIG. 1 may be referred to as a cochlear implant system because sound processor 104 is configured to direct cochlear implant 108 to generate and apply electrical stimulation representative of audio content (e.g., one or more audio signals) to one or more stimulation sites within the patient by way of one or more of electrodes 112.

As shown in FIG. 1, a battery assembly 116 may be included in or otherwise electrically coupled to sound processor 104. Battery assembly 116 may be configured to supply operating power to various components within sound processor 104. In some examples, battery assembly 116 may be configured to be selectively coupled to sound processor 104 (e.g., by inserting battery assembly 116 into a receptacle of sound processor 104). To this end, battery assembly 116 and sound processor 104 may each include interface components (e.g., conductive pins and/or receptacles) and/or interface circuitry configured to facilitate selective coupling therebetween. In some examples, such interface components and/or circuitry may not be configured to facilitate data communication between battery assembly 116 and sound processor 104. This may prevent accidental or intentional programming of either sound processor 104 or battery assembly 116. For example, by not allowing data communication between battery assembly 116 and sound processor 104, a signal from sound processor 104 may not inadvertently cause battery assembly 116 to enter a power-down mode.

Figure 2:
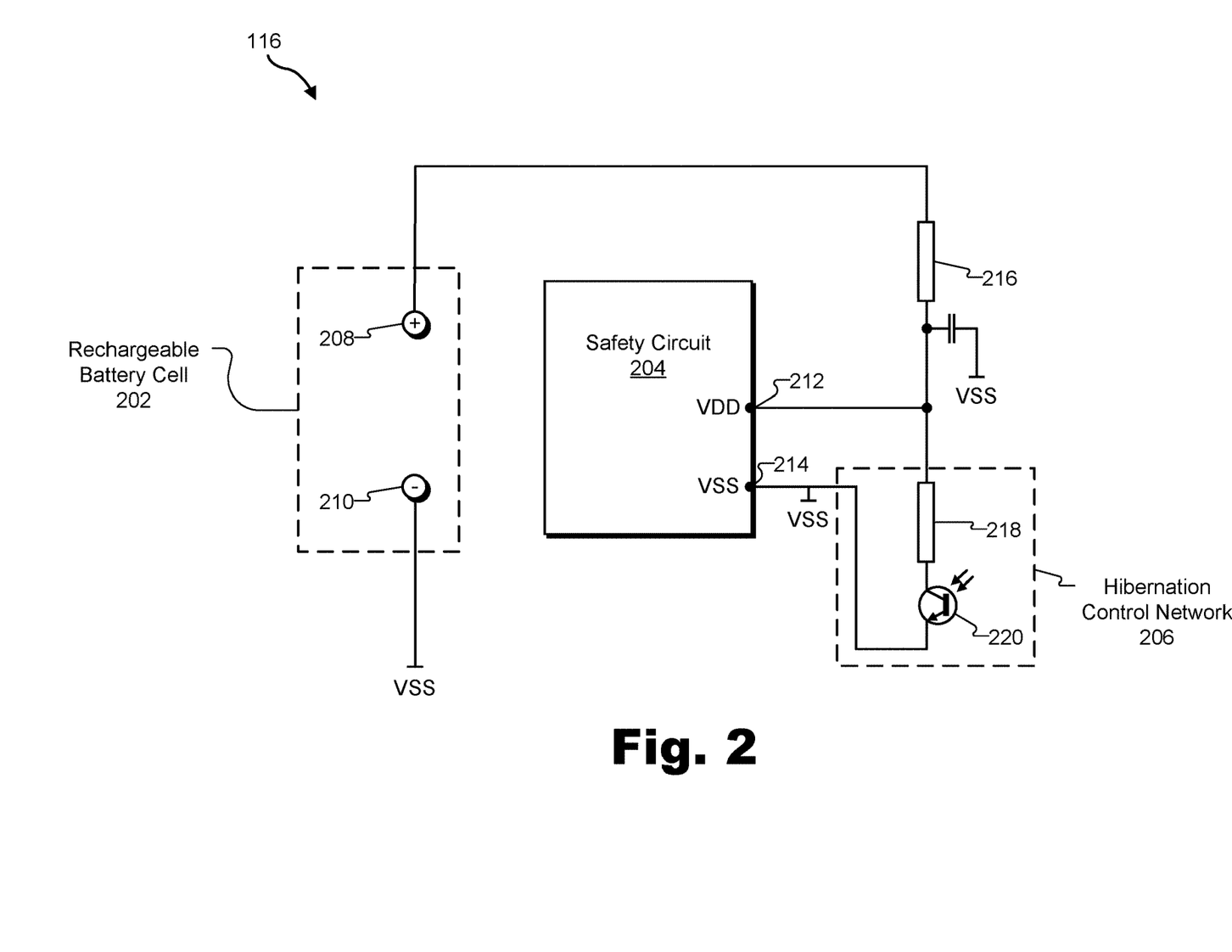
FIG. 2 illustrates an exemplary implementation of a battery assembly according to principles described herein.

FIG. 2 shows an exemplary implementation of battery assembly 116. As shown, battery assembly 116 may include a rechargeable battery cell 202, a safety circuit 204, and a hibernation control network 206. Each of these components will now be described in more detail.

Rechargeable battery cell 202 may include one or more electrical battery cells that may configured to maintain or hold a certain amount of charge that may be used to provide operating power (e.g., for one or more components external to battery assembly 116). As mentioned, the amount of charge that rechargeable battery cell 202 actually has at any given time compared to a maximum amount of charge that rechargeable battery cell 202 is capable of maintaining is referred to as a state of charge. Rechargeable battery cell 202 may be recharged (e.g., by a battery charger) at any time (e.g., after at least some of its charge has been depleted) to increase its state of charge.

Rechargeable battery cell 202 may include a lithium-ion battery cell, a lithium polymer battery cell, and/or any other type of rechargeable battery cell as may suit a particular implementation. Rechargeable battery cell 202 may have any suitable capacity as may serve a particular implementation. In some examples, rechargeable battery cell 202 may be configured specifically for use by a medical device (e.g., wearable medical device, such as sound processor 104) and may therefore have a maximum capacity of 100 milliamp-hours (mAh). As shown in FIG. 2, rechargeable battery cell 202 may include a positive terminal 208 associated with a positive voltage supply provided by rechargeable battery cell 202 and a negative terminal 210 associated with a negative or reference voltage supply provided by rechargeable battery cell 202.

Safety circuit 204 may be configured to perform various safety operations with respect to rechargeable battery cell 202. For example, safety circuit 204 may be configured to transition battery assembly 116 to a power-down mode when the state of charge of rechargeable battery cell 202 is less than a predetermined threshold state or charge (e.g., less than ten percent state of charge). This may be accomplished, for example, by disabling one or more components within battery assembly 116, disconnecting terminals 208 and 210 from a load, and/or in any other manner.

Safety circuit 204 may be implemented in any suitable manner. For example, safety circuit 204 may be implemented by an integrated circuit (e.g., a S-8211C Series Battery Protection IC for 1-Cell Pack by SII SEMICONDUCTOR CORP.). In these implementations, safety circuit 204 may include various input and output terminals. For example, FIG. 2 shows that safety circuit 204 may include a positive voltage supply input terminal 212 labeled VDD ("VDD terminal 212") and a negative voltage supply input terminal 214 labeled VSS ("VSS terminal 214"). It will be recognized that safety circuit 204 may include additional or alternative input and output terminals as may serve a particular implementation.

Safety circuit 204 may be electrically coupled to rechargeable battery cell 202 in any suitable manner. For example, positive terminal 208 of rechargeable battery cell 202 (i.e., a positive voltage supply provided by rechargeable battery cell 202) may be electrically coupled to VDD terminal 212 of safety circuit 204 by way of a resistor 216, and negative terminal 210 of rechargeable battery cell 202 (i.e., a negative or reference voltage supply provided by rechargeable battery cell 202) may be electrically coupled to VSS terminal 214 of safety circuit 204.

In scenarios where battery assembly 116 is actively providing operating power to an external component (e.g., while battery assembly 116 is electrically connected to a sound processor included in a cochlear implant system), safety circuit 204 may actively monitor the actual state of charge of rechargeable battery cell 202. If, during this period of active monitoring, safety circuit 204 detects that the state of charge of rechargeable battery cell 202 goes below a predetermined threshold state of charge (e.g., a ten percent state of charge), safety circuit 204 may transition battery assembly 116 to the power-down mode by, for example, electrically disconnecting terminals 208 and 210 from the external component and/or otherwise preventing battery assembly 116 from providing operating power to the external component. In this manner, safety circuit 204 may prevent the state of charge of rechargeable battery cell 202 from going below the critical state of charge threshold before battery assembly 106 is recharged.

In scenarios where battery assembly 116 is not being used to provide operating power to an external component (e.g., while battery assembly 116 is located in inventory prior to being connected to an external component), safety circuit 204 may still actively or periodically monitor the state of charge of rechargeable battery cell 202 and transition battery assembly 116 to the power-down mode if the state of charge goes below the predetermined threshold state of charge. However, as will be described in more detail below, hibernation control network 206 may "trick" safety circuit 204 into detecting that the state of charge of rechargeable battery cell 202 is below the predetermined threshold state of charge even though the actual state of charge of rechargeable battery cell 202 is above the predetermined threshold state of charge. In this case, safety circuit 204 may determine that the detected state of charge is below the predetermined threshold state of charge (even though the actual state of charge of rechargeable battery cell 202 is above the predetermined threshold state of charge), and, in response, deactivate at least a portion of safety circuit 204.

Safety circuit 204 may detect the state of charge of rechargeable battery cell 202 in any suitable way. For example, safety circuit 204 may detect the state of charge of rechargeable battery cell 202 by detecting a voltage differential between VDD terminal 212 and VSS terminal 214. The detected voltage differential corresponds to the state of charge of rechargeable battery cell 202 and may therefore be used to represent the state of charge of rechargeable battery cell 202. Hence, if the detected voltage differential is below a predetermined voltage differential threshold for a predetermined duration of time, safety circuit 204 may determine that the state of charge of rechargeable battery cell 202 is below the predetermined threshold state of charge.

Alternatively, if needed, the detected voltage differential may be compared to a predetermined discharge curve of rechargeable battery cell 202, and then translated (e.g., by safety circuit 204) into an estimated state of charge of rechargeable battery cell 202. In some examples, safety circuit 204 may consider additional or alternative factors in determining the state of charge of rechargeable battery cell 202 including, but not limited to, a usable capacity of rechargeable battery cell 202, a charge—discharge rate of rechargeable battery cell 202, a hysteresis of the charge—discharge rate of rechargeable battery cell 202, a charge efficiency (e.g., coulombic efficiency, charge acceptance, etc.) of rechargeable battery cell 202, a present and/or historic temperature of rechargeable battery cell 202, an age of rechargeable battery cell 202, a number of charge—discharge cycles of rechargeable battery cell 202, a self-discharge rate of rechargeable battery cell 202, and/or any other factors as may suit a particular implementation.

Safety circuit 204 may compare the detected state of charge to the predetermined threshold state of charge. The predetermined threshold state of charge may be any suitable value (e.g., ten percent) as may serve a particular implementation. If the detected state of charge is below the predetermined state of charge for a predetermined duration of time (e.g., for more than a couple seconds), safety circuit may transition battery assembly 116 to the power-down mode.

Hibernation control network 206 may be configured to trigger, at the direction of an external user, safety circuit 204 to transition battery assembly 116 into the power-down mode even if the state of charge of rechargeable battery cell 202 is above the predetermined threshold state of charge. As will be described below, hibernation control network 206 may do this by indicating to safety circuit 204 that the state of charge of rechargeable battery cell 202 is below the predetermined threshold state of charge even though the state of charge of rechargeable battery cell 204 is actually still above the predetermined threshold state of charge.

As shown in FIG. 2, hibernation control network 206 may be electrically connected to safety circuit 204 in series between VDD terminal 212 and VSS terminal 214. Hibernation control network 206 may include a resistor 218 and a phototransistor 220 in series one with another. As shown, resistor 218 is also electrically coupled to VDD terminal 212 and phototransistor 220 is also electrically coupled to VSS terminal 214.

Phototransistor 220 may be configured to operate as a light-controlled switch. While in an open state, phototransistor 220 may prevent current from flowing between VDD terminal 212 and VSS terminal 214. While in a closed state, resistor 218 may be shorted to VSS terminal 214 by way of phototransistor 220.

Phototransistor 220 may be configured to transition from the open state to the closed state in response to detecting a light beam having a predetermined wavelength and emitted by a light source located external to battery assembly 116. The predetermined wavelength may, for example, be in a near-infrared portion of an electromagnetic spectrum (e.g., 940 nm).

To illustrate, an external user may point a light beam having the predetermined wavelength and emitted by a light source (e.g., a near-infrared transmitter) at phototransistor 220. In response to detecting the light beam for a predetermined duration of time (e.g., 0.5 seconds), phototransistor 220 may transition from the open state to the closed state. In some examples, this predetermined duration of time may be related to (e.g., equal or proportional to) the duration of the time that safety circuit 204 needs to detect a voltage differential between VDD terminal 212 and VSS terminal 214 that causes safety circuit 204 to transition battery assembly 116 to the power-down mode. Alternatively, if phototransistor 220 is exposed to a light source having a wavelength that is not equal to the predetermined wavelength, phototransistor 220 will not transition from the open state to the closed state.

Additionally or alternatively, phototransistor 220 may be configured to transition from the open state to the closed state in response to being exposed to light that has a set of one or more other predefined attributes. For example, phototransistor 220 may be configured to transition from the open state to the closed state in response to being exposed to light having an intensity above a predetermined intensity threshold, light having a predetermined polarization, light emitted by a particular light source, etc.

While phototransistor 220 is in the closed state, resistor 218 is shorted to VSS terminal 214. Resistance values of resistor 216 and resistor 218 may be selected such that they cause, while resistor 218 is shorted to VSS terminal 214, a voltage at VDD terminal 212 to be such that the voltage differential between VDD terminal 212 and VSS terminal 214 is below the predetermined voltage differential threshold, even though the actual state of charge of rechargeable battery cell 202 is above the predetermined state of charge threshold. This may trigger safety circuit 204 to transition battery assembly 116 to the power-down mode while the actual state of charge of rechargeable battery cell 202 is still greater than the predetermined state of charge threshold.

As mentioned, safety circuit 204 may transition battery assembly 116 to the power-down mode by deactivating a portion of safety circuit 204. For example, safety circuit 204 may transition battery assembly 116 to the power-down mode by deactivating all components of safety circuit 204 except for an input voltage circuit and a comparator, which may remain active in order to perform other safety functions associated with battery assembly 116. By deactivating a portion of safety circuit 204 in this manner, the self-discharge rate of rechargeable battery cell 202 may be reduced up to at least ninety percent. This, in turn, may extend the shelf life of battery assembly 116 from a few months to up to at least twenty-four months.

In some embodiments, the resistance values of resistor 216 and resistor 218 may prevent the voltage differential between VDD terminal 212 and VSS terminal 214 from being below the predetermined voltage differential threshold when the actual state of charge of rechargeable battery cell 202 is greater than another predetermined state of charge that is higher than the predetermined state of charge, regardless of whether phototransistor 220 is in the closed state.

By way of illustration, the another predetermined state of charge may be fifty percent. In this example, if rechargeable battery cell 202 has a state of charge of sixty percent and phototransistor 220 detects, for a suitable time duration, a light beam having the predetermined wavelength, phototransistor 220 may transition from the open state to the closed state. However, even with phototransistor 220 in the closed state, the resistance values of resistor 216 and 218 may prevent the voltage differential between VDD terminal 212 and VSS terminal 214 from being below the predetermined voltage differential threshold. Because the voltage differential between VDD terminal 212 and VSS terminal 214 is not below the predetermined voltage differential threshold, safety circuit 204 will not transition battery assembly 116 to the power-down mode. This may be beneficial in scenarios where incidental exposure to a light beam having the predetermined wavelength will not cause battery assembly 116 to enter the power-down mode.

For example, incidental exposure of a light beam having the predetermined wavelength to phototransistor 220 while battery assembly 116 is providing operating power to a sound processor included in a cochlear implant system will not cause battery assembly 116 to enter the power-down mode (which would in turn shut the sound processor down) if the state of charge of rechargeable battery cell 202 is greater than a particular threshold amount (e.g., fifty percent).

Figure 3:
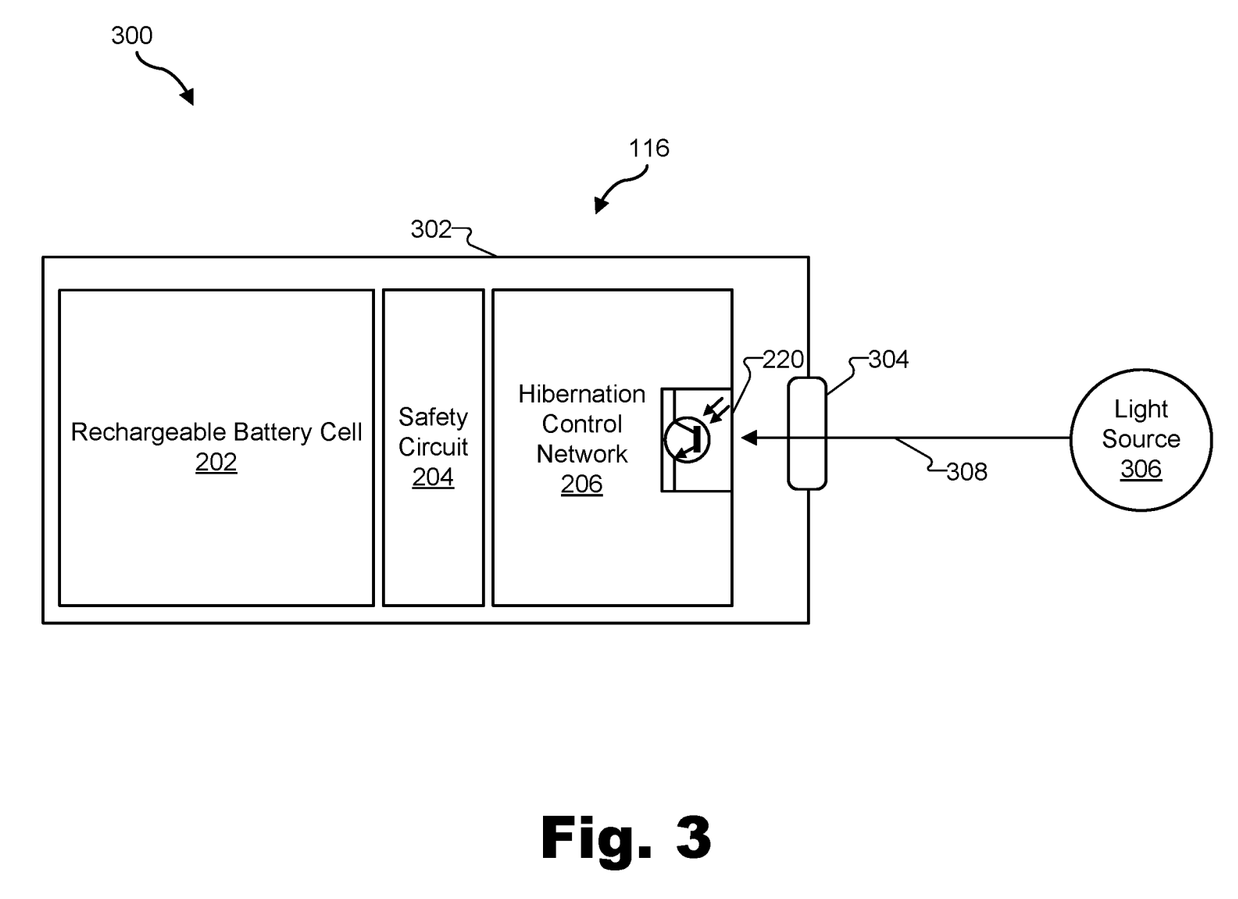
FIG. 3 shows an exemplary implementation in which the battery assembly illustrated in FIG. 2 further includes a housing with a window configured to allow a phototransistor that is enclosed by the housing to detect light beams according to principles described herein.

FIG. 3 illustrates an implementation 300 in which battery assembly 116 includes a housing 302 that encloses rechargeable battery cell 202, safety circuit 204, and hibernation control network 206. As shown, housing 302 includes a window 304.

Window 304 may be made out of any suitable material configured to allow phototransistor 220 to detect, while phototransistor 220 is enclosed within housing 302, light beams having the predetermined wavelength. For example, FIG. 3 shows that a light source 306 external to housing 302 of battery assembly 116 that is emitting a light beam 308. As shown, light beam 308 passes through window 304 and is received by phototransistor 220. As mentioned, if light beam 308 has an appropriate wavelength and is received by phototransistor 220 for at least a predetermined amount of time, phototransistor 220 may enter a closed state. This, in turn, may trigger safety circuit 204 to transition battery assembly 116 into the power-down mode as described above. It will be recognized that light source 306 may be operated by any suitable user (e.g., a person managing an inventory of battery assemblies).

In some examples, window 304 is disposed on an interface side of housing 302. As used herein, an "interface side" refers to a side of housing 302 that faces sound processor 104 when battery assembly 116 is connected to sound processor 104. For example, the interface side of housing 302 may be inserted into a receptacle of sound processor 104. In this manner, while battery assembly 115 is connected to sound processor 104, window 304 may be hidden from view, thereby preventing accidental exposure to light that may trigger safety circuit 204 to transition battery assembly 116 into the power-down mode.

Safety circuit 204 may also, subsequent to the transition of battery assembly 116 into the power-down mode, transition (e.g., restore) battery assembly 116 to a normal operation mode (i.e., a mode in which safety circuit 204 is actively or periodically monitoring the state of charge of rechargeable battery cell 202). For example, while battery assembly 116 is in the power-down mode, a user may connect battery assembly 116 to a suitable battery charger. Safety circuit 204 may detect that battery assembly 116 is connected to the battery charger in any suitable manner. In response, safety circuit 204 may transition battery assembly 116 to the normal operational mode. Battery assembly 116 may include any suitable components to facilitate a connection between battery assembly 116 and a battery charger.

Safety circuit 204 may transition battery assembly 116 to the normal operation mode by enabling one or more disabled components within battery assembly 116 (e.g., activating a deactivated portion of safety circuit 204), connecting disconnected terminals 208 and/or 210 to a load, and/or in any other manner. Subsequent to the transition of battery assembly 116 to the normal operation mode, and after attaining a sufficient state of charge (e.g., a state of charge greater than the predetermined state of charge threshold) by way of the battery charger, battery assembly 116 may again be used to provide operating power to an external component.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A battery assembly comprising:
    a housing;
    a rechargeable battery cell in the housing and that has a state of charge;
    a safety circuit in the housing and electrically coupled to the rechargeable battery cell, the safety circuit configured to transition the battery assembly to a power-down mode when the state of charge of the rechargeable battery cell is less than a predetermined threshold state of charge;
    a hibernation control network in the housing and electrically coupled to the safety circuit, the hibernation control network comprising a phototransistor, wherein the hibernation control network is configured to:
        detect, by way of the phototransistor while the state of charge of the rechargeable battery cell is greater than the predetermined threshold state of charge, a light beam having a predetermined wavelength and emitted by a light source located external to the battery assembly; and
        trigger, in response to the detection of the light beam of the predetermined wavelength, the safety circuit to transition the battery assembly to the power-down mode while the state of charge of the rechargeable battery cell is still greater than the predetermined threshold state of charge; and
    a window on a side of the housing and configured to allow the phototransistor to detect, through the window, the light beam emitted by the light source located external to the housing.

2. The battery assembly of claim 1, wherein the rechargeable battery cell is a lithium-ion battery cell.

3. The battery assembly of claim 1, wherein the predetermined wavelength is in a near-infrared region of an electromagnetic spectrum.

4. The battery assembly of claim 1, wherein the safety circuit is configured to transition the battery assembly to the power-down mode by:
    detecting the state of charge of the rechargeable battery cell;

determining that the detected state of charge is below the predetermined threshold state of charge; and deactivating, in response to the determining that the detected state of charge is below the predetermined threshold state of charge, a portion of the safety circuit.

5. The battery assembly of claim 4, wherein the hibernation control network is configured to trigger the safety circuit to transition the battery assembly to the power-down mode by indicating to the safety circuit that the state of charge of the rechargeable battery cell is below the predetermined threshold state of charge even though the state of charge of the rechargeable battery cell is still above the predetermined threshold state of charge.

6. The battery assembly of claim 4, wherein:

the safety circuit comprises an integrated circuit comprising:
    a positive voltage supply ("VDD") terminal connected to a positive voltage supply provided by the rechargeable battery cell, and
    a negative voltage supply ("VSS") terminal connected to a reference voltage supply, and the phototransistor is electrically coupled to the safety circuit in series between the VDD terminal and the VSS terminal.

7. The battery assembly of claim 6, wherein the safety circuit is configured to determine that the state of charge is below the predetermined threshold state of charge by detecting that a voltage differential between the VDD terminal and the VSS terminal is below a predetermined voltage differential threshold for a predetermined duration of time.

8. The battery assembly of claim 7, wherein:

the safety circuit further comprises a first resistor that is electrically coupled in series between a positive terminal of the rechargeable battery cell and the VDD terminal; and the hibernation control network further comprises a second resistor that is electrically coupled in series between the phototransistor and the VDD terminal;

wherein, when the hibernation control network detects, by way of the phototransistor, the light beam for a second predetermined duration of time, the hibernation control network shorts the second resistor by way of the phototransistor to the VSS terminal; and wherein the first and second resistors have resistance values that cause, while the second resistor is shorted to the VSS terminal, a voltage at the VDD terminal to be such that the voltage differential between the VDD terminal and the VSS terminal is below the predetermined voltage differential threshold.

9. The battery assembly of claim 8, wherein:

the resistance values of the first and second resistors prevent the voltage differential between the VDD terminal and the VSS terminal from being below the predetermined voltage differential threshold while the state of charge of the rechargeable battery cell is greater than another predetermined threshold state of charge that is higher than the predetermined threshold state of charge.

10. The battery assembly of claim 9, wherein the another predetermined state of charge is fifty percent state of charge.

11. The battery assembly of claim 1, wherein, subsequent to the transition of the battery assembly into the power-down mode, the safety circuit is configured to:

detect that the battery assembly is connected to a battery charger, and in response to the detection that the battery assembly is connected to the battery charger, transition the battery assembly to a normal operation mode.

12. A method comprising:

detecting, by a hibernation control network included in a battery assembly and through a window of a housing of the battery assembly, a light beam having a predetermined wavelength and emitted by a light source located external to the housing of the battery assembly, the battery assembly further comprising a rechargeable battery cell that has a state of charge and a safety circuit configured to transition the battery assembly to a power-down mode when the state of charge of the rechargeable battery cell is less than a predetermined threshold state of charge, wherein the detecting is performed while the state of charge is greater than the predetermined threshold state of charge; and triggering, by the hibernation control network, in response to the detecting of the light beam of the predetermined wavelength and while the state of charge of the rechargeable battery is still greater than the predetermined threshold state of charge, the safety circuit to transition the battery assembly to the power-down mode.

13. The method of claim 12, wherein:

the rechargeable battery cell is a Lithium Ion battery cell;

the predetermined wavelength is in a near-infrared region of an electromagnetic spectrum; and the triggering comprises indicating to the safety circuit that the state of charge of the rechargeable battery cell is below the predetermined threshold state of charge even though the state of charge of the rechargeable battery cell is still above the predetermined threshold state of charge.

* * * * *